United States Patent [19]
Stein et al.

[11] Patent Number: 5,243,979
[45] Date of Patent: Sep. 14, 1993

[54] METHOD AND APPARATUS FOR IMPLEMENTING ACTIVITY SENSING IN A PULSE GENERATOR

[75] Inventors: Paul M. Stein, Maple Grove; David L. Thompson, Fridley, both of Minn.

[73] Assignee: Medtronic, Inc., Minneapolis, Minn.

[21] Appl. No.: 794,766

[22] Filed: Nov. 15, 1991

[51] Int. Cl.⁵ .............................................. A61N 1/36
[52] U.S. Cl. ...................................................... 607/20
[58] Field of Search ...................... 128/419 PG, 419 R

[56] References Cited

U.S. PATENT DOCUMENTS

| | | | |
|---|---|---|---|
| 4,257,423 | 3/1981 | McDonald et al. | 128/419 PG |
| 4,305,397 | 12/1981 | Weisbrod et al. | 128/419 PT |
| 4,323,074 | 4/1982 | Nelms | 128/419 PG |
| 4,379,459 | 4/1983 | Stein | 128/419 PG |
| 4,428,378 | 1/1984 | Anderson et al. | 128/419 PG |
| 4,467,807 | 8/1984 | Bornzin | 128/419 PG |
| 4,476,868 | 10/1984 | Thompson | 128/419 PL |
| 4,485,813 | 12/1984 | Anderson et al. | 128/675 |
| 4,550,370 | 10/1985 | Baker | 364/413 |
| 4,556,063 | 12/1985 | Thompson et al. | 128/419 PT |
| 4,730,618 | 3/1988 | Lekholm et al. | 128/419 PG |
| 4,750,495 | 6/1988 | Moore et al. | 128/419 PG |
| 4,807,629 | 2/1989 | Baudino et al. | 128/419 PG |
| 4,817,606 | 4/1989 | Lekholm | 128/419 PG |
| 4,917,115 | 4/1990 | Flammang et al. | 128/419 PG |
| 4,926,863 | 5/1990 | Alt | 128/419 PG |
| 4,932,408 | 6/1990 | Shaldach | 128/419 PG |
| 5,031,615 | 7/1991 | Alt | 128/419 PG |
| 5,040,534 | 8/1991 | Mann et al. | 128/419 PG |
| 5,052,388 | 10/1991 | Sivula et al. | 128/419 PG |
| 5,080,096 | 1/1992 | Hooper et al. | 128/419 R |
| 5,097,831 | 3/1992 | Lekholm | 128/419 PG |
| 5,127,404 | 7/1992 | Wyborny et al. | 128/419 P |

Primary Examiner—Lee S. Cohen
Assistant Examiner—Jeffrey R. Jastrzab
Attorney, Agent, or Firm—Dwight N. Holmbo; Harold R. Patton

[57] ABSTRACT

A cardiac pacemaker of the type including a sensor responsive to the patient's metabolic demand for oxygenated blood and which varies the pacing rate in response to the output of the sensor. In the disclosed embodiment, a piezoelectric sensor bonded to the inside surface of the pacemaker's outer shield delivers a pulsatile sensor signal to activity circuitry, where the different peak values of the pulsatile signal correspond to different levels of patient activity. The activity circuit defines a plurality of sensor signal threshold levels. Rate control circuitry increases the pacing rate of the pacemaker by amounts corresponding to the threshold level exceeded by recent peak values of said pulsatile signal; peaks of said pulsatile signal which exceed only the lowest of the thresholds cause the smallest increase in the pacing rate, while sensor signals which exceed higher thresholds cause larger increases in the pacing rate. Several parameters, including upper and lower pacing rate limits and rate-response settings are selectable by means of an external programming device communicating with the pacemaker via radio-frequency telemetry.

8 Claims, 5 Drawing Sheets

METHOD AND APPARATUS FOR IMPLEMENTING ACTIVITY SENSING IN A PULSE GENERATOR

FIELD OF THE INVENTION

This invention relates generally to the field of cardiac pacemakers, and more particularly relates to cardiac pacemakers of the type which measure the metabolic demand for oxygenated blood and vary the pacing rate of the pacemaker in accordance therewith.

BACKGROUND OF THE INVENTION

A wide variety of cardiac pacemakers are known and commercially available. Pacemakers are generally characterized by which chambers of the heart they are capable of sensing, the chambers to which they deliver pacing stimuli, and their responses, if any, to sensed intrinsic electrical cardiac activity. Some pacemakers deliver pacing stimuli at fixed, regular intervals without regard to naturally occurring cardiac activity. More commonly, however, pacemakers sense electrical cardiac activity in one or both of the chambers of the heart, and inhibit or trigger delivery of pacing stimuli to the heart based on the occurrence and recognition of sensed intrinsic electrical events. A so-called "VVI" pacemaker, for example, senses electrical cardiac activity in the ventricle of the patient's heart, and delivers pacing stimuli to the ventricle only in the absence of electrical signals indicative of natural ventricular contractions. A "DDD" pacemaker, on the other hand, senses electrical signals in both the atrium and ventricle of the patient's heart, and delivers atrial pacing stimuli in the absence of signals indicative of natural atrial contractions, and ventricular pacing stimuli in the absence of signals indicative of natural ventricular contractions. The delivery of each pacing stimulus by a DDD pacemaker is synchronized with prior sensed or paced events.

Pacemakers are also known which respond to other types of physiologically-based signals, such as signals from sensors for measuring the pressure inside the patient's ventricle or for measuring the level of the patient's physical activity. In recent years, pacemakers which measure the metabolic demand for oxygen and vary the pacing rate in response thereto have become widely available. Perhaps the most popularly employed method for measuring the need for oxygenated blood is to measure the physical activity of the patient by means of a piezoelectric transducer. Such a pacemaker is disclosed in U.S. Pat. No. 4,485,813 issued to Anderson et al. Alternatively, oxygen saturation may be measured directly as disclosed in U.S. Pat. No. 4,467,807 issued to Bornzin, U.S. Pat. No. 4,807,629 issued to Baudino et al., and in U.S. Pat. No. 4,750,495 issued to Brumwell et al. Other parameters employed to measure the metabolic demand for oxygenated blood include right ventricular blood pressure and the change of right ventricular blood pressure over time, venous blood temperature, respiration rate, minute ventilation, and various pre- and post-systolic time intervals measured by impedance or pressure sensing within the right ventricle of the heart.

In typical prior art rate-responsive pacemakers, the pacing rate is determined according to the output from an activity sensor. The pacing rate is variable between a predetermined maximum and minimum level, which may be selectable by a physician from among a plurality of programmable upper and lower rate limit settings. When the activity sensor output indicates that the patient's activity level has increased, the pacing rate is increased accordingly. As long as patient activity continues to be indicated, the pacing rate is periodically increased by some incremental amount, until the programmed upper rate limit is reached. When patient activity ceases, the pacing rate is gradually reduced, until the programmed lower rate limit is reached.

A piezoelectric crystal is typically fixed to the pacemaker shield and generates an electrical signal in response to deflections of the pacemaker shield caused by patient activity. Piezoelectric, microphone-like sensors are widely used in rate-responsive pacemakers because they are relatively inexpensive, their manufactured yield is high, and they transduce the acoustic energy of patients' motion in a highly reliable manner.

In one prior art technique for employing a piezoelectric, microphone-like sensor for transducing patient activity, the raw electrical signal output from the sensor is applied to an AC-coupled system which bandpass filters the signal prior to being applied to pacemaker rate-setting logic. This arrangement is disclosed, for example, in U.S. Pat. No. 5,052,388 to Sivula et al., assigned by the assignee of the present invention and incorporated herein by reference. According to the Sivula et al. reference, peaks in the bandpass filtered sensor signal which exceed a predetermined threshold are interpreted by the rate-setting logic as an indication of patient activity of sufficient magnitude that an increase in the pacing rate may be warranted. The predetermined threshold, which may also be selectable by a physician from one of a plurality of programmable settings, is intended to screen out background "noise" in the sensor output signal indicative of low amplitude patient motion. Each occurrence of a peak in the bandpass-filtered sensor signal which exceeds the threshold level is known as an activity count. A sum of activity counts is computed over some period of time; for example, the number of activity counts may be determined every two seconds. If, at the end of that period, the number of activity counts exceeds some predetermined value, the ratesetting logic interprets this as an indication that the pacing rate should be incrementally increased.

In the utilization of sensor signals in the manner just described, for a given threshold setting, the rate-setting logic does not distinguish between different levels of physical activity; that is, each activity count is weighted equally, and the magnitude of each activity count has no bearing upon the rate-setting logic's processing of that count. An activity count which greatly exceeds the threshold setting is treated no differently than one that just barely exceeds the threshold. As a result, the pacing rate may be increased by the same amount whether the patient is engaged in vigorous or only moderate levels of physical activity.

SUMMARY OF THE INVENTION

In the embodiment of the invention disclosed herein, a piezoelectric microphone-like activity sensor is employed which produces a raw sensor output signal. The sensor output signal is bandpass-filtered and differentiated, and then applied to the input of a multiple-tier threshold detection circuit. The threshold detection circuit produces a plurality of output signals. Each of the plurality of output signals is assigned a weight value, so that upon each assertion of any given output signal, the corresponding weight value is added to a running sum of activity counts. At any given time, the running sum corresponds to the sum of weighted activity counts which have occurred during the previous two seconds.

An Activity Count value is computed by cumulating and averaging the previous six seconds' worth of two-second running sums (i.e., the previous three running sums), and this Activity Count value is used in determining an appropriate pacing rate for the amount and magnitude of detected patient activity.

In the disclosed embodiment of the invention, the pacemaker is programmable by means of an external programming device, so that certain parameters and values may be selected by a physician after implant of the device. The physician can program, for example, the upper and lower limits on the pacing rate, the threshold below which patient activity does not lead to increases in the rate-responsive pacing rate, the desired rate response setting (e.g. low, medium, or high), the desired rate response slope, and so on.

BRIEF DESCRIPTION OF THE DRAWINGS

The foregoing and other features of the present invention will be best appreciated with reference to the detailed description of a specific embodiment of the invention, which follows, when read in conjunction with accompanying drawings, wherein:

FIG. 5b is a graph of the pacing rate of the pacemaker of FIGS. 1 and 2 during the time intervals of FIG. 5a; and FIG. 5c is a graph of the pacing rate of a prior art pacemaker during the time intervals of FIG. 5a.

DETAILED DESCRIPTION OF A SPECIFIC EMBODIMENT OF THE INVENTION

Figure 1:
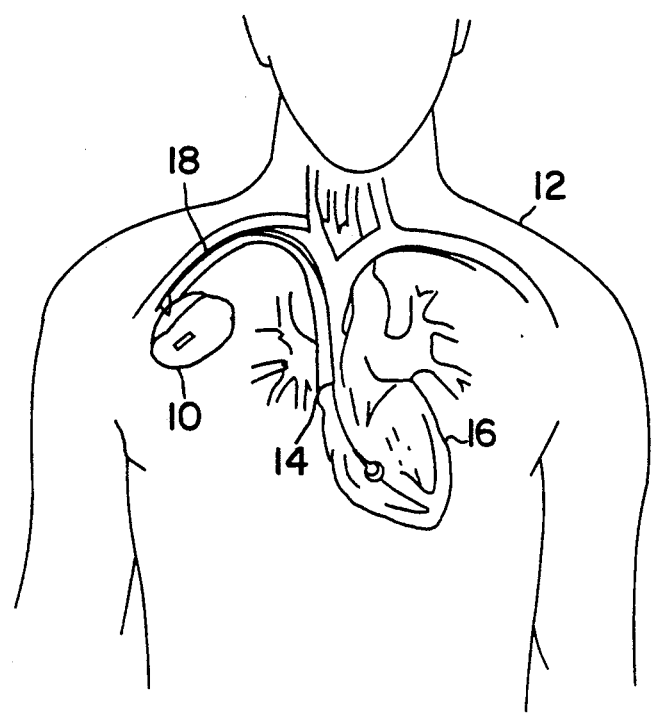
FIG. 1 is a diagram showing the placement in the patient of a pacemaker in accordance with one embodiment of the present invention.

FIG. 1 shows generally where a pacemaker 10 in accordance with one embodiment of the present invention may be implanted in a patient 12. It is to be understood that pacemaker 10 is contained within a hermetically-sealed, biologically inert outer shield or "can", in accordance with common practice in the art. A pacemaker lead 14 is electrically coupled to pacemaker 10 and extends into the patient's heart 16 via a vein 18. The distal end of lead 14 includes one or more exposed conductive electrodes for receiving electrical cardiac signals and/or for delivering electrical pacing stimuli to the heart 16.

Figure 2:
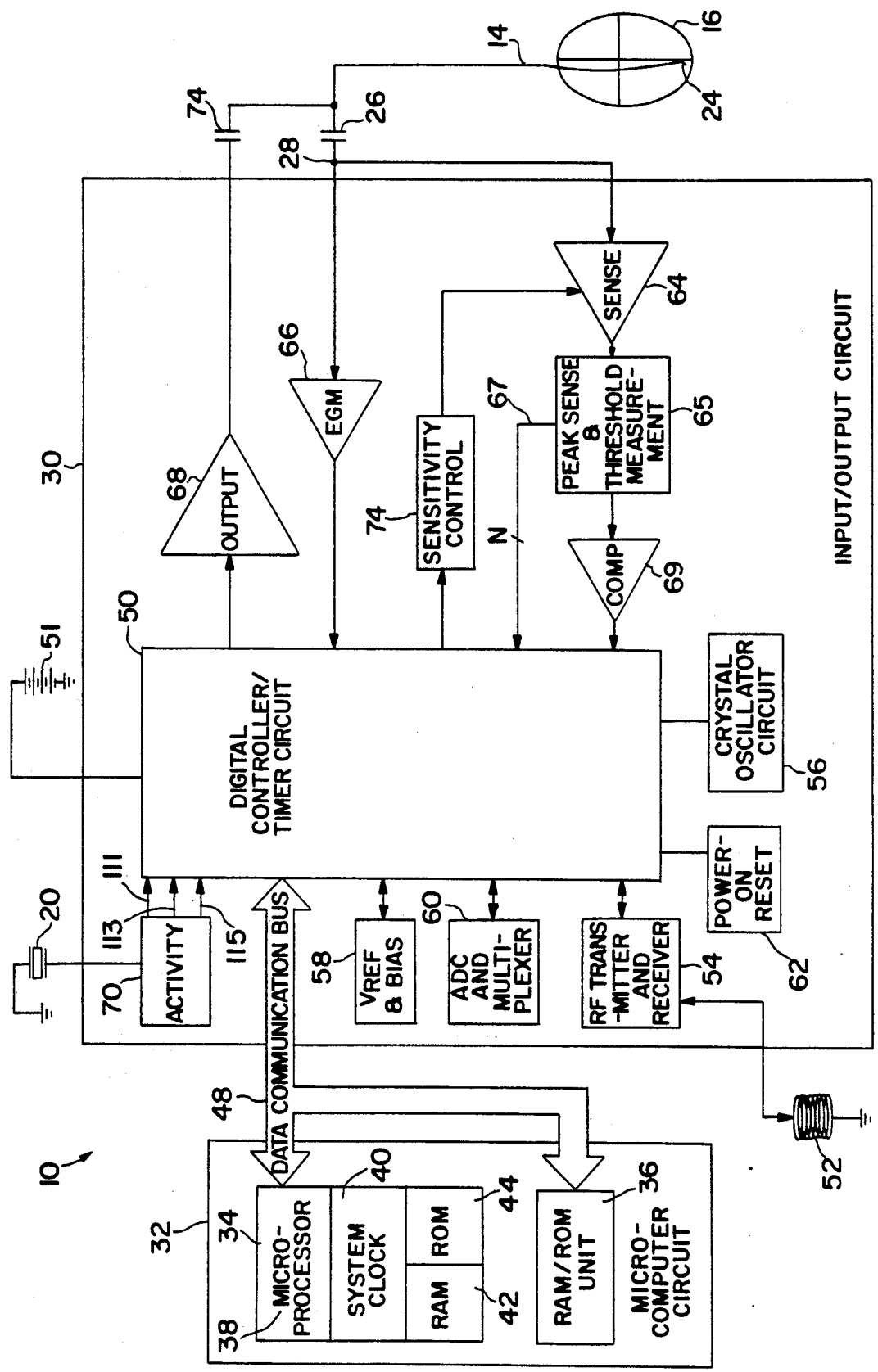
FIG. 2 is a block diagram of functional components of the pacemaker of FIG. 1.

Turning now to FIG. 2, a block diagram of pacemaker from FIG. 1 is shown. Although the present invention will be described herein in conjunction with a pacemaker 10 having a microprocessor-based architecture, it will be understood that pacemaker 10 may be implemented in any logic based, custom integrated circuit architecture, if desired. It will also be understood that the present invention may be utilized in conjunction with other implantable medical devices, such as cardioverters, defibrillators, cardiac assist systems, and the like.

In the illustrative embodiment shown in FIG. 2, pacemaker 10 includes an activity sensor 20, which may be, for example, a piezoelectric element bonded to the inside of the pacemaker's shield. Such a pacemaker/activity sensor configuration is the subject of the above-referenced patent to Anderson et al., which is hereby incorporated by reference in its entirety. Piezoelectric sensor 20 provides a sensor output which varies as a function of a measured parameter that relates to the metabolic requirements of patient 12.

Pacemaker 10 of FIG. 2 is programmable by means of an external programming unit (not shown in the Figures). One such programmer suitable for the purposes of the present invention is the Medtronic Model 9710 programmer which has been commercially available for several years and is intended to be used with all Medtronic pacemakers. The programmer is a microprocessor device which provides a series of encoded signals to pacemaker 10 by means of a programming head which transmits radio-frequency (RF) encoded signals to pacemaker 10 according to the telemetry system laid out, for example, in U.S. Pat. No. 4,305,397 issued to Weisbrod et al. on Dec. 15, 1981, U.S. Pat. No. 4,323,074 issued to Nelms on Apr. 6, 1982, or in U.S. Pat. No. 4,550,370 issued to Baker on Oct. 29, 1985, all of which are hereby incorporated by reference in their entirety. It is to be understood, however, that the programming methodologies disclosed in the above-referenced patents are identified herein for the purposes of illustration only, and that any programming methodology may be employed so long as the desired information is transmitted to the pacemaker. It is believed that one of skill in the art would be able to choose from any of a number of available programming techniques to accomplish this task.

The programmer facilitates the selection by a physician of the desired parameter to be programmed and the entry of a particular setting for the desired parameter. For purposes of the present invention, the specifics of operation of the programmer are not believed to be important with the exception that whatever programmer is used must include means for selecting an upper rate (UR), a lower rate (LR), and one of a plurality of rate response (RR) settings to be hereinafter described in greater detail.

In the illustrative embodiment, the lower rate may be programmable, for example from 40 to 90 pulses per minute (PPM) in increments of 10 PPM, the upper rate may be programmable between 100 and 175 PPM in 25 PPM increments, and there may be 10 rate response functions, numbered one through ten, available.

In addition, the programmer may include means for selection of acceleration and deceleration parameters which limit the rate of change of the pacing rate. Typically, these parameters are referred to in rate responsive pacemakers as acceleration and deceleration settings, respectively, or attack and decay settings, respectively. These may be expressed in terms of the time interval required for the pacemaker to change between the current pacing rate and 90% of the desired pacing interval, assuming that the activity level corresponding to the desired pacing rate remains constant. Appropriate selectable values for the acceleration time would be, for example, 0.25 minutes, 0.5 minutes, and 1 minute. Appropriate selectable values for the deceleration time would be, for example, 2.5 minutes, 5 minutes, and 10 minutes.

Pacemaker 10 is schematically shown in FIG. 2 to be electrically coupled via a pacing lead 14 to a patient's heart 16. Lead 14 includes an intracardiac electrode 24 located near its distal end and positioned within the right ventricular (RV) or right atrial (RA) chamber of heart 16. Lead 14 can carry either unipolar or bipolar electrodes as is well known in the art. Although an application of the present invention in the context of a single-chamber pacemaker will be disclosed herein for illustrative purposes, it is to be understood that the present invention is equally applicable in dual-chamber pacemakers.

Electrode 24 is coupled via suitable lead conductor 14 through input capacitor 26 to node 28 and to input-/output terminals of an input/output circuit 30. In the presently disclosed embodiment, activity sensor 20 is bonded to the inside of the pacemaker's outer protective shield, in accordance with common practice in the art. As shown in FIG. 2, the output from activity sensor 20 is coupled to input/output circuit 30.

Input/output circuit 30 contains the analog circuits for interface to the heart 16, activity sensor 20, antenna 52, as well as circuits for the application of stimulating pulses to heart 16 to control its rate as a function thereof under control of the software-implemented algorithms in a microcomputer circuit 32.

Microcomputer circuit 32 comprises an on-board circuit 34 and an off-board circuit 36. On-board circuit 34 includes a microprocessor 38, a system clock circuit 40, and on-board RAM 42 and ROM 44. In the presently disclosed embodiment of the invention, off-board circuit 36 includes a RAM/ROM unit. On-board circuit 34 and off-board circuit 36 are each coupled by a data communication bus 48 to a digital controller/timer circuit 50. Microcomputer circuit 32 may be fabricated of a custom integrated circuit device augmented by standard RAM/ROM components.

It will be understood that the electrical components represented in FIG. 1 are powered by an appropriate implantable battery power source 51, in accordance with common practice in the art. For the sake of clarity, the coupling of battery power to the various components of pacemaker 10 has not been shown in the Figures.

An antenna 52 is connected to input/output circuit 30 for purposes of uplink/downlink telemetry through RF transmitter and receiver unit 54. Unit 54 may correspond to the telemetry and program logic employed in U.S. Pat. No. 4,566,063 issued to Thompson et al. on Dec. 3, 1985 and U.S. Pat. No. 4,257,423 issued to McDonald et al. on Mar. 4, 1981, both of which are incorporated herein by reference in their entirety. Telemetering analog and/or digital data between antenna 52 and an external device, such as the aforementioned external programmer (not shown), may be accomplished in the presently disclosed embodiment by means of all data first being digitally encoded and then pulse-position modulated on a damped RF carrier, as substantially described in co-pending U.S. Pat. application Ser. No. 468,407, filed on Jan. 22, 1990, entitled "Improved Telemetry Format", which is assigned to the assignee of the present invention and which is incorporated herein by reference. The particular programming and telemetry scheme chosen is not believed to be important for the purposes of the present invention so long as it provides for entry and storage of values of rate-response parameters discussed herein.

A crystal oscillator circuit 56, typically a 32,768-Hz crystal-controlled oscillator, provides main timing clock signals to digital controller/timer circuit 50. A $V_{REF}$ and Bias circuit 58 generates stable voltage reference and bias currents for the analog circuits of input-/output circuit 30. An analog-to-digital converter (ADC) and multiplexer unit 60 digitizes analog signals and voltages to provide "real-time" telemetry intracardiac signals and battery end-of-life (EOL) replacement function. A power-on-reset (POR) circuit 62 functions as a means to reset circuitry and related functions to a default condition upon detection of a low battery condition, which will occur upon initial device power-up or will transiently occur in the presence of electromagnetic interference, for example.

The operating commands for controlling the timing of pacemaker 10 are coupled by bus 48 to digital controller/timer circuit 50 wherein digital timers and counters are employed to establish the overall escape interval of the pacemaker, as well as various refractory, blanking, and other timing windows for controlling the operation of the peripheral components within input-/output circuit 30.

Digital controller/timer circuit 50 is coupled to sensing circuitry including a sense amplifier 64, a peak sense and threshold measurement unit 65, and a comparator/-threshold detector 69. Circuit 50 is further coupled to an electrogram (EGM) amplifier 66 for receiving amplified and processed signals picked up from electrode 24 through lead conductor 14 and capacitor 26 representative of the electrical activity of the patient's heart 16. Sense amplifier 64 amplifies sensed electrical cardiac signals and provides this amplified signal to peak sense and threshold measurement circuitry 65, which provides an indication of peak sensed voltages and the measured sense amplifier threshold voltage on multiple conductor signal path 67 to digital controller/timer circuit 50. The amplified sense amplifier signal is then provided to comparator/threshold detector 69. Sense amplifier 64 may correspond, for example, to that disclosed in U.S. Pat. No. 4,379,459 issued to Stein on Apr. 12, 1983, incorporated by reference herein in its entirety. The electrogram signal developed by EGM amplifier 66 is used on those occasions when the implanted device is being interrogated by an external programmer, not shown, to transmit by uplink telemetry a representation of the analog electrogram of the patient's electrical heart activity, such as described in U.S. Pat. No. 4,556,063, issued to Thompson et al., assigned to the assignee of the present invention and incorporated herein by reference. An output pulse generator 68 provides pacing stimuli to the patient's heart 16 through coupling capacitor 74 in response to a pacing trigger signal developed by digital controller/timer circuit 50 each time the escape interval times out, or an externally transmitted pacing command has been received, or in response to other stored commands as is well known in the pacing art. Output amplifier 68 may correspond generally to the output amplifier disclosed in U.S. Pat. No. 4,476,868 issued to Thompson on Oct. 16, 1984 also incorporated herein by reference in its entirety.

While specific embodiments of input sense amplifier 64, output amplifier 68, and EGM amplifier 66 have been identified herein, this is done for the purposes of illustration only. It is believed by the inventor that the specific embodiments of such circuits are not critical to the present invention so long as they provide means for generating a stimulating pulse and provide digital controller/timer circuit 50 with signals indicative of natural and/or stimulated contractions of the heart.

Figure 3:
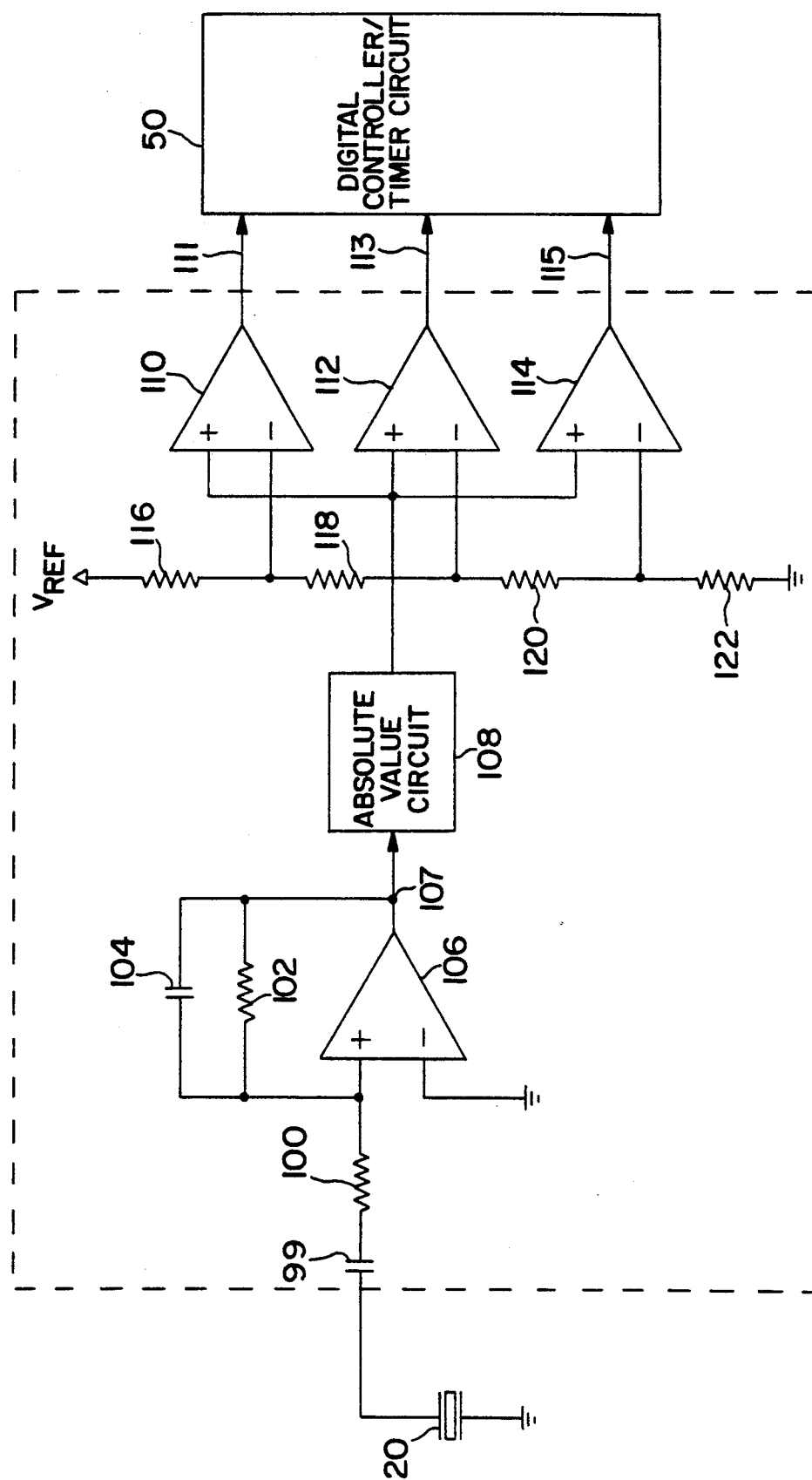
FIG. 3 is a schematic diagram of the activity circuit from FIG. 2.

Digital controller/timer circuit 50 is coupled to an activity circuit 70 for receiving, processing, and amplifying signals received from activity sensor 20. In FIG. 3, a schematic diagram of activity circuit 70 from FIG. 2 is shown. Activity circuit 70 produces a plurality of activity signals which are collectively representative of the patient's metabolic requirements, as shall be hereinafter described. As shown in FIG. 3, activity circuit 70 includes resistors 100 and 102, capacitors 99 and 104, and amplifier 106, which collectively perform bandpass filtering, amplification, and differentiation upon the raw output signal from piezoelectric activity sensor 20. The processed signal on line 107 is then applied to an absolute value circuit 108, which performs a full-wave rectification of the processed piezoelectric sensor output signal. The specific implementation of absolute value circuit 108 will not be discussed herein, as it is believed by the inventor that implementation of an absolute value circuit would be a matter of routine to a person of ordinary skill in the art. An absolute value circuit suitable for the purposes of the present invention is disclosed in the above-reference Anderson patent.

The output of circuit 108 is applied to a first input to each of three one-shot voltage comparators 110, 112, and 114. Coupled to a second input to each of the comparators 110, 112, and 114 are reference voltages derived from the voltage divider comprising resistors 116, 118, 120, and 122. As would be apparent to one of ordinary skill in the art, resistors 116, 118, 120, and 122 are coupled between a reference voltage source $V_{REF}$ (provided from $V_{REF}$/Bias circuit 58 shown in FIG. 2) and ground, so that a different reference voltage is applied to comparators 110, 112, and 114, with the reference voltage applied to comparator 110 being greater than that applied to comparator 112, and the reference voltage applied to comparator 112 being greater than that of 114. This arrangement results in a three-tiered voltage comparison, with the respective reference voltage applied to each one of the comparators 110, 112, and 114 defining an input signal threshold. For each of the comparators 110, 112, and 114, an input signal to that comparator which is below that comparator's reference (threshold) voltage will cause the output of that comparator to have a zero value, while an input signal above the corresponding reference (threshold) voltage will cause the output of that comparator to have a positive value. A sufficiently low voltage on line 108 will exceed only the threshold level of comparator 114, a medium voltage on line 108 will exceed the threshold level of comparators 112 and 114 but not comparator 110, and a sufficiently high voltage on line 108 will exceed the threshold level of comparators 110, 112, and 114. Thus, activity sensor 70 is capable of distinguishing between three magnitudes of activity sensor signal peaks. The output signals on lines 111, 113, and 115 define three classes of activity counts, corresponding to "low" activity levels (indicated by signals on line 115), "medium" activity levels (indicated by signals on line 113), and "high" activity levels (indicated by signals on line 111).

It will be understood by those skilled in the art, however, that the output signal from activity sensor 20 can alternatively be coupled to signal processing circuitry to derive a current-based output, rather than a voltage-based output. For example, a transconductance amplifier coupled to activity sensor 20 via a suitable bandpass filter and differentiator would provide such alternative current-based output which varies its current level as a function of the patient's activity. Accordingly, suitable current level detectors provided with a suitable current reference would be substituted in place of voltage comparators 110, 112, and 114, for level detection of the appropriately absolute valued output signal.

Although activity circuit 70 is capable of distinguishing between three magnitudes of activity sensor signal peaks, it is contemplated by the inventor that any number of tiered voltage comparisons may be carried out by activity circuit 70 by simply providing an appropriate number of threshold-detecting comparators therein. It is believed by the inventor that, in view of the present disclosure, adapting the present invention to include a different number of tiered voltage comparisons would be a matter of routine to one of ordinary skill in the art.

Figure 4A:
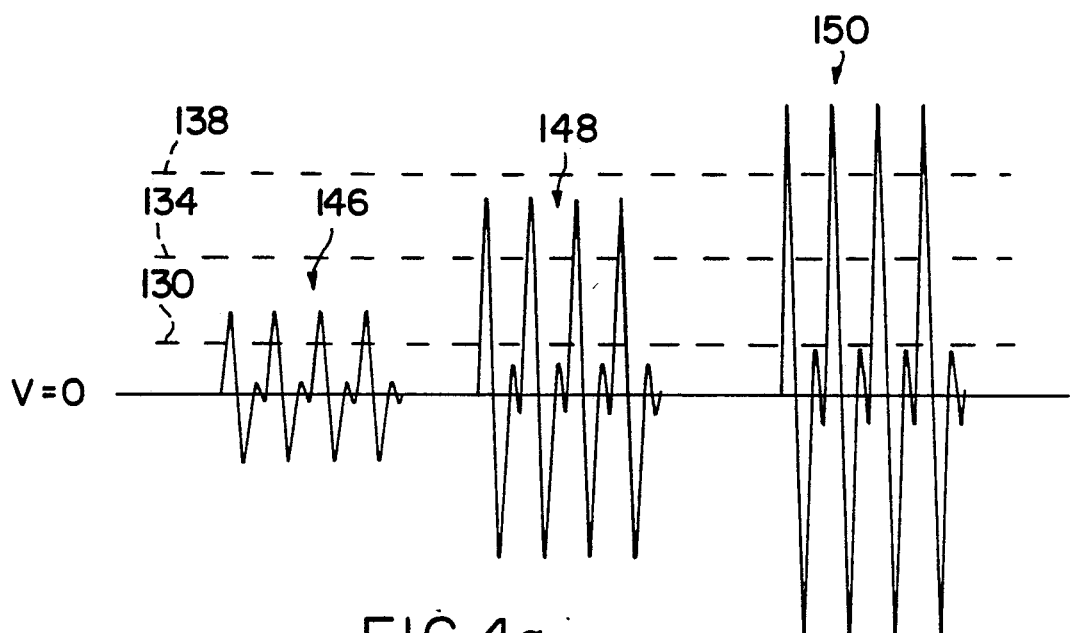
FIG. 4a is a graph of voltage versus time of hypothetical signals applied to the activity circuit of FIGS. 2 and 3.

Turning now to FIG. 4a, a voltage versus time graph of hypothetical electrical output signals from sensor 20 is shown, with depictions of the respective threshold levels defined by comparators 110, 112, and 114 of FIG. 3 also being provided. As would be apparent to one of ordinary skill in the art, the output signal from a piezoelectric sensor output signal is a complex waveform that may generally be characterized as pulsatile in nature when generated in response to repetitive movement such as walking or running. It is to be understood, therefore, that the hypothetical signals depicted in FIGS. 4a and 4b are merely simplified representations of piezoelectric output signals, and these representations are provided herein solely for the purposes of describing the operation of activity circuit 70.

Figure 4B:
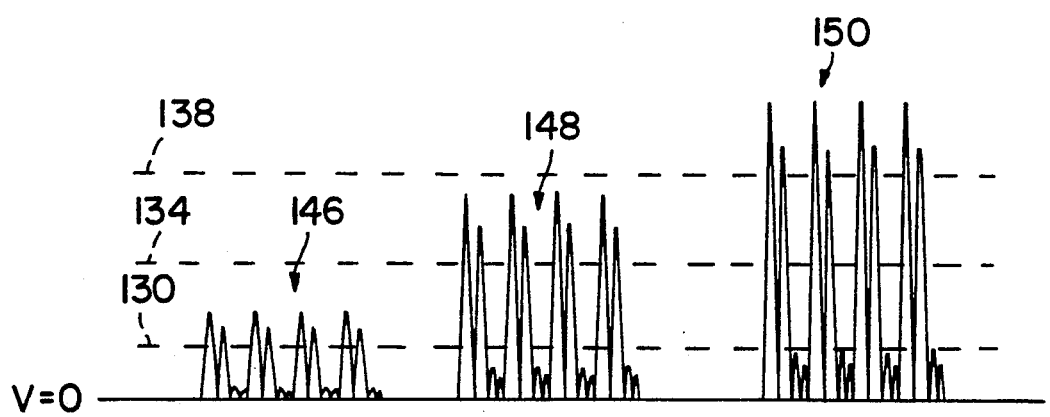
FIG. 4b is a graph of voltage versus time of the hypothetical signals of FIG. 4a after passing through the absolute value circuit of FIG. 3.

In FIGS. 4a and 4b, dashed line 130 represents the activity threshold voltage (that is, the threshold voltage of comparator 114 in FIG. 3). Dashed line 134 represents a magnitude-two sensing threshold (that is, the threshold voltage of comparator 112). Similarly, dashed lines 138 represents a magnitude-three sensing threshold (the threshold voltage of comparator 110).

After the signals from FIG. 4a are applied to absolute value circuit 108, they are transformed into the form shown in FIG. 4b, wherein negative excursions of the signals in FIG. 4a (i.e. excursions below the zero voltage V = axis) have been transformed into positive voltage excursions.

Considering first the series of lower-level signals designated generally as 146 in FIG. 4b, such signals (if produced by piezoelectric sensor 20) would be construed, in accordance with the presently disclosed embodiment of the invention, as being indicative of the lowest level of activity to which the presently disclosed pacemaker will respond. Each time threshold 130 is exceeded this constitutes an activity count having an assigned weight of one. Thus, in the series of peaks 146, activity threshold 130 is exceeded eight times, resulting in an activity count value of eight and a weighted activity count value of eight (eight times the weight factor of one). The signals denoted generally as 148 in FIG. 4b would be construed, if generated by piezoelectric sensor 20, as being indicative of medium levels of activity. Each time threshold 134 is exceeded this constitutes an activity count having a weighted value of two. Since signals 148 exceed activity threshold 134 a total of eight times, signals 148 would result in an activity count of eight and a weighted activity count of sixteen (eight times the weight factor of two). Likewise, the signals denoted generally as 150 in FIG. 4, if generated by activity sensor 20 and applied to rate circuit 70, would be construed as being indicative of the highest level of patient activity recognized by the presently disclosed pacemaker. Each time threshold 138 is exceeded constitutes an activity count having a weighted value of four. The series of peaks 150 exceeds threshold 138 eight times, resulting in a weighted activity count of thirty-two (eight times the weight factor of four).

In accordance with the presently disclosed embodiment of the invention, microprocessor 34 (FIG. 2) computes an average over a period of six seconds of the weighted activity count values computed during those six seconds, where the weighted activity count values are computed every two seconds. That is, every two seconds, microprocessor 34 adds the three most recently computed activity count values and divides by three to yield a six-second average of weighted activity counts, this six second average being designated Activity Count in the following formulas. The rate-responsive pacing rate is then determined according to the following Activity Rate Function:

$$\text{ACTIVITY RATE FUNCTION} = \frac{1}{K} \times \frac{60}{\text{CLOCKS}} \times \left[ \frac{32768}{328} \right] \quad (1)$$

where K is a constant based upon the outputs from comparitors 110, 112 and 114, the value (32,768/328) corresponds to the number of cycles per second of the system clock, and CLOCKS represents the number of system clock cycles in the desired rate-responsive pacing interval, determined according to the formula:

$$\text{CLOCKS} = \frac{C}{\text{ACTIVITY COUNT} + D} \quad (2)$$

with C and D defined as follows:

$$C = \frac{(2 \times d)}{e} \quad (3)$$

$$D = \left( \frac{h}{e} \right) \quad (4)$$

d, e, and h being defined as follows:

$$d = \frac{(108 \times U_T \times L_T)}{(L_T - U_T)} \quad (5)$$

$$e = \text{programmed value (range 3-12)} \quad (6)$$

$$h = \frac{(216 \times U_T)}{(L_T - U_T)} \quad (7)$$

and where $L_{96}$ and $U_T$ correspond to selectable Lower and Upper rates values and are determined according to the following Tables 1 and 2:

TABLE 1

| LOWER RATE | $L_T$ |
|---|---|
| 40 PPM | 149 |
| 50 PPM | 119 |
| 60 PPM | 96 |
| 70 PPM | 85 |
| 80 PPM | 74 |

TABLE 1-continued

| LOWER RATE | $L_T$ |
|---|---|
| 90 PPM | 66 |

TABLE 2

| UPPER RATE | $U_T$ |
|---|---|
| 100 PPM | 59 |
| 110 PPM | 53 |
| 120 PPM | 49 |
| 130 PPM | 45 |
| 140 PPM | 42 |
| 150 PPM | 39 |
| 160 PPM | 36 |
| 170 PPM | 34 |

A peripheral (programmer), not shown in the FIGS. performs the calculations from equations 2-7 above upon programming or initiating rate responsive pacing. The values of K, C, and D in the equations are telemetered to pacemaker 10 via antenna 52 and Input/Output circuit 30 and stored in RAM 42 or RAM/ROM unit 36. Microprocessor 34 performs the calculation from Equation 1 above periodically, for example once every two seconds.

The programmed value "e" according to equation (6) above represents a selection from among ten possible families of rate-response functions available in the pacemaker of the present invention. As described herein, the "e" factor corresponds to the so-called "rate response setting" discussed at length in the above-referenced patent to Sivula et al. As the Sivula et al. has been incorporated herein by reference in its entirety, the effect of the "e" factor will not be further discussed herein.

In equation (1) above, the term 1/K is a scaling factor which affects the pacing rate which will be reached in response to a particular level of detected activity. In the presently disclosed embodiment of the invention, K can take on one of three possible values, namely $K_1 = 0.86$, $K_2 = 0.63$, or $K_3 = 0.46$, resulting in (1/K) values of approximately 1.16, 1.59, and 2.17, respectively. Each time microprocessor 34 performs the computation set forth in equation (1), microprocessor 34 will utilize either $K_1$, $K_2$, or $K_3$ depending upon which of the threshold levels 130, 134, or 138 has been exceeding during the preceding two-second interval. For example, if during a given two-second interval, threshold 134 but not threshold 138 has been exceeded, microprocessor 34 will utilize $K_2$ in the computation of equation (1). If threshold 138 has been exceeded during the two-second interval, $K_3$ will be utilized. The effect of the 1/K scaling factor will be hereinafter discussed in greater detail.

Figure 5A:
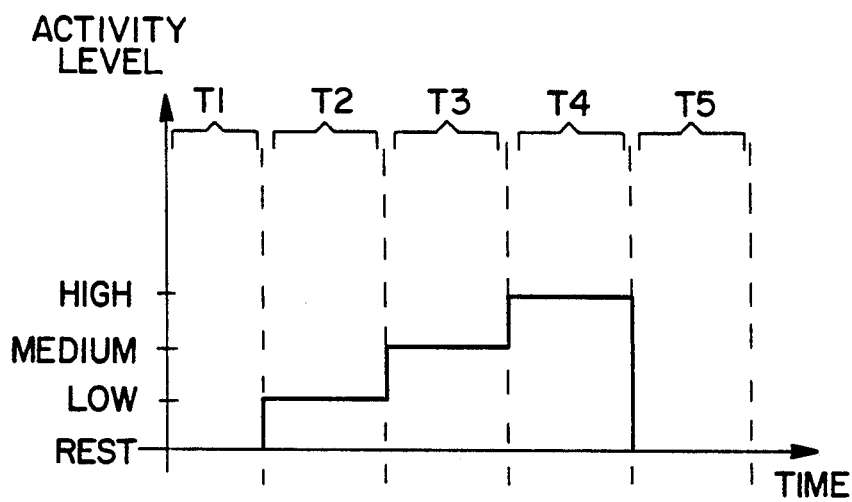
FIG. 5a is a graph of the level of patient activity over several time intervals.
Figure 5B:
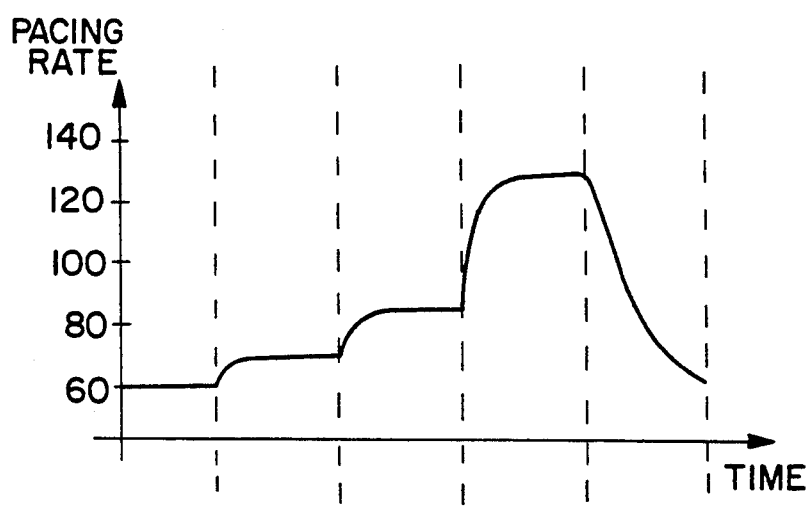

Turning now to FIGS. 5a and 5b, graphs showing the relationship between detected levels of activity and the rate-responsive pacing rate of pacemaker 10, in accordance with the presently disclosed embodiment of the invention, are shown. In the following discussion of FIGS. 5a, 5b, and 5c, it will be assumed for the purposes of illustration that a lower pacing rate limit of 60 PPM and an upper pacing rate limit of 130 PPM have been programmed. In FIGS. 5a and 5b, five time intervals designated as T1, T2, T3, T4, and T5 are separated by dashed lines. During time interval T1, the patient is assumed to be at rest, with Activity Count equal to zero as shown in FIG. 5a (see equation 2 above) and the pacing rate at the programmed lower rate limit of 60 PPM as shown in FIG. 5b. During time interval T2, only low-level patient activity has been detected and the Activity Count has a low-level but non-zero value. As a result, as shown in FIG. 5b, the pacing rate is increased during time interval T2 to a higher rate than during time T1. Detection of low-level patient activity causes the pacing rate to be gradually increased from 60 PPM up to approximately 70 PPM. This is shown in FIG. 5b during time interval T2.

The 70 PPM limit on the response to low-level activity is brought about through the effect of the scaling factor 1/K in equation (1). As long as only low-level patient activity is detected during time interval T2, (that is, the sensor output signal exceeds only the threshold of comparator 114), the value $K_1$ will be utilized by microprocessor 34 when performing the computation of equation (1).

During time interval T3, medium-level patient activity has been detected, as shown in FIG. 5a. As shown in FIG. 5b, the pacing rate is increased during T3 to approximately 90 PPM in response to detection of medium-level patient activity. So long as only medium-level activity is detected (that is, only the thresholds of comparators 114 and 112 are exceeded), the pacing rate will not be increased above 90 PPM. Again, the 90 PPM limit on the response to detected medium level activity is brought about through the effect of 1/K. During time T3, medium-level patient activity has been detected, so that $K_2$ will be used in performing the calculation of equation (1).

During time interval T4, high-level patient activity is detected, as shown in FIG. 5a. As can be seen from FIG. 5b, detection of high-level patient activity causes an increase in the pacing rate up to the programmed upper rate limit of 130 PPM. When high-level activity is detected during a two-second period, microprocessor 34 will utilize $K_3$ when performing the computation of equation (1).

Finally, during time interval T5, no patient activity is detected; the Activity Count during time interval T5 goes to zero, and the pacing rate is reduced to its lower rate value, as shown in FIG. 5b.

Although specific values for the maximum pacing rate at various levels of patient activity (e.g. 70 PPM for low-level activity, 90 PPM for medium-level patient activity, and so on), specific values for $L_T$, and $U_T$, and specific values for $K_1$, $K_2$, and $K_3$ have been identified herein, these values are given for the purposes of illustration only, and it is to be understood that these values may be varied depending upon particular applications of the present invention, and upon such factors as the programmed upper and lower rate limits, the programmed rate response setting, the desired relationship between maximum pacing rates in response to different levels of detected activity, and so on. For example, if it is desired that the pacing rate limit in response to low-level, medium-level, and high-levels of detected patient activity be values other than 70, 90, and 130, respectively, different values for $K_1$, $K_2$, and $K_3$ may be defined.

Figure 5C:
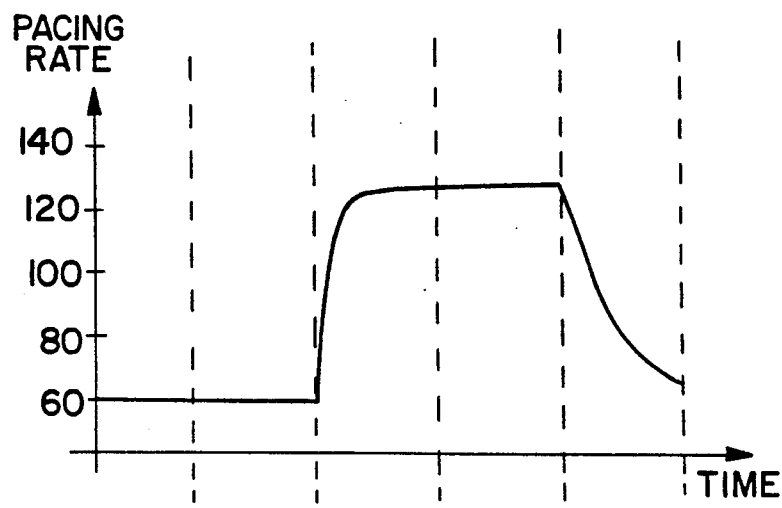

So that some of the distinguishing qualities of the present invention over the prior art may be better appreciated, the graph of FIG. 5c shows the response of a prior art pacemaker to the activity levels depicted in FIG. 5a. The pacemaker whose response is shown in FIG. 5c may be, for example, the commercially-available Medtronic Activitrax TM or Legend TM pacemakers, or the like, which are not capable of distinguishing between multiple activity levels. With prior art pacemakers such as the Activitrax TM, the increase in the pacing rate in response to detected activity is initiated only once, when detected activity exceeds the single activity threshold of the pacemaker, during time interval T3. It is believed to be physiologically advantageous for the pacing rate of a rate responsive pacemaker to be increased in the more gradual or incremental manner depicted in FIG. 5b than in the more abrupt, one-time manner depicted in FIG. 5c.

Just as prior art pacemakers allowed for the selection of one of a number of rate response settings, pacemaker is in accordance with the presently disclosed embodiment of the invention is capable of being programmed into one of three rate-response settings: high, medium, and low. In prior art rate-responsive pacemakers, the programmable rate response setting determined the single threshold level below which sensor output would not effect the pacemaker's rate. In the presently disclosed embodiment of the invention, on the other hand, the rate response setting determines not one but three threshold levels, one for each of comparators 110, 112, and 114.

One way of expressing the thresholds of comparators 110, 112, and 114 is in terms of the amount of pressure which must be exerted on piezoelectric sensor 20 in order for a particular threshold to be reached. It follows, therefore, that less pressure is required to be exerted on sensor 20 to exceed the threshold of comparator 114 than is required to exceed the threshold of comparator 112, and so on. While the exact values of the threshold voltages of comparators 110, 112, and 114 will vary according to the type of activity sensor used, the effect of bandpass amplifier 106, and so on, the inventor's presently preferred embodiment of the invention is based on a 111-pascal force exerted on sensor 20. Normalizing 111 to 1, the low, medium, and high rate-response settings for the presently disclosed embodiment of pacemaker 10 may be expressed in the following Table 3:

TABLE 3

| RATE RESPONSE SETTING | LOW ACTIVITY THRESHOLD | MEDIUM ACTIVITY THRESHOLD | HIGH ACTIVITY THRESHOLD |
| --- | --- | --- | --- |
| Low | 1/8 | 1/4 | 3/8 |
| Medium | 3/8 | 1/2 | 5/8 |
| High | 5/8 | 1 | 1 1/4 |

The values in Table 3 are interpreted as multipliers of the value 111. For example, in the medium rate response setting, the low activity threshold (the threshold of comparator 114) corresponds to a pressure of three-eighths times 111 pascals (i.e., approximately 41.6 pascals) being exerted on sensor 20; the medium activity threshold (the threshold of comparator 112) corresponds to a pressure of one-half times 111 pascals (i.e., 55.5 pascals) being exerted on sensor 20; and the high activity threshold (the threshold of comparator 110) corresponds to a pressure of five-eighths times 111 pascals (i.e., approximately 69.4 pascals) being exerted on sensor 20.

From the foregoing detailed description of a specific embodiment of the invention, it should be apparent that a rate-responsive pacemaker has been disclosed which is capable of automatically adjusting its pacing rate in response to detection of patient activity at various activity levels. While a particular embodiment of the present invention has been disclosed in detail, it is to be understood that this has been done for illustrative purposes only, and should not be taken as a limitation upon the scope of the present invention. It is contemplated by the inventor that various alterations, substitutions, and modifications to the disclosed embodiment may be made without departing from the spirit and scope of the invention as set forth in the appended claims.

For example, while the present disclosure relates to a single chamber pacemaker which would operate in the VVIR or AAIR mode, the invention is also equally applicable to dual chamber pacemakers of all types, including DDDR, DDIR, VDDR and DVIR type pacemakers. In such embodiments, various interval-based parameters may be varied as a function of the sensor-based output signals to alter the pacemaker's operation as desired, such as by varying the following: the interval between atrial pacing pulses (DVIR and DDDR); the interval between ventricular pacing pulses (DDDR, DDIR, VDDR, and DVIR); the interval between a ventricular pulse and the next subsequent atrial pacing pulse (DDDR, DDIR, and DVIR); the interval between the atrial and ventricular pulses (DDDR, DDIR, and DVIR); and/or other pacing-related intervals which may be sensor-varied, such as the post-ventricular atrial refractory period (PVARP) and the upper rate limit interval (URL). Moreover, the present invention is also believed to be useful in the context of multiple sensor pacemakers, in which the pacing rate is determined by a plurality of measured physical parameters. In such embodiments, the desired rate-responsive pacing interval for one sensor might be combined with the desired rate-responsive pacing interval for another sensor by weighted or unweighted averaging or by other methods.

Thus, the present specification should be regarded as exemplary, rather than limiting in nature, with regard to the following claims.

What is claimed is:

1. A pacemaker, enclosed within a housing, comprising:
   rate control means for producing a triggering signal;
   a pulse generator adapted to be coupled to a patient's heart, and further coupled to said rate control means, said pulse generator responsive to said triggering signal from said rate control means to generate a pacing pulse;
   an activity sensor adapted to be coupled to said patient, said sensor producing an output signal having a signal level which varies as a function of patient activity; and
   an activity circuit, coupled to said activity sensor and to said rate control means, said activity circuit comprising a plurality of threshold detector means for detecting signal levels that exceed predetermined threshold levels, each of said detector means defining a different threshold level than others of said plurality of threshold detector means and each one of plurality of threshold detector means receiving said output signal;
   such that for a time-variant excursion of said output signal to a peak signal level, each one of said threshold detector means having a threshold lower than said peak signal level produces an output pulse in response to said signal excursion;
   said rate control means comprising:
   means for counting said output pulses;
   computing means responsive to said output pulses, said computing means assigning a weighted count value for each said output pulse, said computing means further calculating a running sum for said weighted count values; and
   adjustment means coupled to said computing means for varying a periodic rate for said triggering signal as a function of said running sum of weighted count values.

2. A pacemaker in accordance with claim 1, wherein said activity sensor comprises a piezoelectric crystal bonded to a wall of said housing so as to produce said output signal in response to deflections of said housing wall.

3. A pacemaker, comprising:
   rate control means for producing a triggering signal;
   a pulse generator adapted to be coupled to a patient's heart, and further coupled to said rate control means, said pulse generator responsive to said triggering signal from said rate control means to generate a pacing pulse;
   an activity sensor adapted to be coupled to said patient, said sensor producing an output signal indicative of patient activity; and
   an activity circuit, coupled to said activity sensor and to said rate control means, said activity circuit comprising a plurality of voltage threshold detector means for detecting signal levels that exceed predetermined threshold levels $\{T_1 \ldots T_N\}$ each defining a threshold voltage $\{V_1 \ldots V_N\}$ where $V_1 < V_2 < \ldots < V4N$, each of said voltage threshold detector means $\{T_1 \ldots T_N\}$ having a corresponding preassigned weight value $\{W_1 \ldots W_N\}$ where $W_1 < W_2 < \ldots < W_N$, and each one of said threshold detector means $\{T_1 \ldots T_N\}$ receiving said output signal,
   such that for a time-variant excursion of said output signal to a peak voltage level $V_P$, each threshold detector means $T_X$ defining a threshold voltage $V_X < V_P$ produces an output pulse in response to said given excursion;
   said rate control means comprising:
   means for counting said output pulses;
   computing means coupled to said output pulses, said computing means assigning a weighted count value for each said output pulse, said computing means further calculating a running sum for said weighted count values; and
   adjustment means coupled to said computing means for varying a periodic rate for said triggering signal as a function of said running sum of weighted count values.

4. A pacemaker in accordance with claim 3, wherein said activity sensor comprises a piezoelectric crystal bonded to a wall of said housing so as to produce an output signal in response to deflections of said wall.

5. A method of pacing a patient's heart, comprising the steps of:
   (a) producing a pulsatile signal indicative of said patient's activity;
   (b) defining a plurality of threshold voltage levels $\{T_1 \ldots T_n\}$ where $T_1 < T_2 < \ldots T_N$, having associated therewith a corresponding plurality of weight values $\{W_1 \ldots W_N\}$ where $W_1 < W_2 < \ldots W_N$;
   (c) for each time-variant excursion of said pulsatile signal exceeding a subset $\{T_1 \ldots T_X\}$ of said plurality of threshold levels, adding $W_X$ to a running sum of weight values;
   (d) delivering pacing pulses to said patient's heart at a variable rate, where said variable rate is determined as a function of said running sum of weight values.

6. A method of selecting a pacing rate for a variable-rate cardiac pacemaker, comprising the steps of:
  (a) producing a pulsatile activity signal indicative of a patient's activity;
  (b) defining a plurality of threshold voltage levels $\{T_1...T_N\}$ where $T_1<T_2<...T_N$, having associated therewith a corresponding plurality of weight values $\{W_1...W_N\}$ where $W_1<W_2<...W_N$;
  (c) resetting a running sum of weight values to zero;
  (d) during a first predetermined time interval, for each time-variant excursion of said pulsatile signal to a peak voltage level exceeding a subset $\{T_1...T_X\}$ of said plurality of threshold levels, adding $W_X$ to said running sum of weight values;
  (e) upon expiration of said predetermined time interval, storing said running sum in a memory;
  (f) repeating steps (c)-(e) M times to yield M of said stored running sums;
  (g) averaging said M running sums to yield an Activity Count;
  (h) computing an Activity Rate Function where:

ACTIVITY RATE FUNCTION =

$$\frac{1}{K} \times \frac{60}{\text{CLOCKS}} \times \left[\frac{32768}{328}\right]$$

where K comprises a scaling factor which varies according to a maximum peak voltage level of said pulsatile signal during said predetermined time interval; and where $$\text{CLOCKS} = \frac{C}{\text{ACTIVITY COUNT} + D}$$

where $$C = \frac{(2 \times d)}{e}$$

and $$D = \left(\frac{h}{e}\right)$$

where $$d = \frac{(108 \times U_T \times L_T)}{(L_T - U_T)}$$

and e is selectable in the range three to twelve, and where $$h = \frac{(216 \times U_T)}{(L_T - U_T)}$$

with $L_T$ and $U_{96}$ corresponding to selected lower and upper rate limits, respectively, where possible values of $L_T$ and $U_T$ and respectively corresponding lower and upper rates are:

| LOWER RATE | $L_T$ |
| --- | --- |
| 40 PPM | 149 |
| 50 PPM | 119 |
| 60 PPM | 96 |
| 70 PPM | 85 |
| 80 PPM | 74 |
| 90 PPM | 66 |
| UPPER RATE | $U_T$ |
| 100 PPM | 59 |
| 125 PPM | 47 |
| 150 PPM | 39 |
| 175 PPM | 22 |

(i) selecting said pacing rate according to said Activity Rate Function; and
  (j) delivering pacing pulses to said patient's heart at said selected pacing rate.

7. A pacemaker, enclosed within a housing, comprising:
  rate control means for producing a triggering signal;
  a pulse generator adapted to be coupled to a patient's heart, and further coupled to said rate control means, said pulse generator responsive to said triggering signal from said rate control means to generate a pacing pulse;
  an activity sensor adapted to be coupled to said patient, said sensor producing a pulsatile output signal indicative of patient activity; and
  an activity circuit, coupled to said activity sensor and to said rate control means, said activity circuit comprising a plurality of voltage threshold detector means for detecting signal levels that exceed predetermined threshold levels $\{T_1...T_N\}$ each defining a threshold voltage $\{V_1...V_N\}$ where $V_1<V_2<...V_N$, each of said voltage threshold detector means $\{T_1...T_N\}$ having a corresponding preassigned weight value $\{W_1...W_N 56$ where $W_1<W_2<...W_N$, and each one of said threshold detector means $\{T_1...T_N\}$ receiving said pulsatile output signal,
  such that for a time-variant excursion of said activity signal to a peak voltage level $V_P$, each threshold detector means $T_X$ defining a threshold voltage $V_X<V_P$ produces an output pulse in response to said excursion;
  said rate control means comprising:
  means for counting said output pulses;
  said computing means adding said weight value for said corresponding threshold detector means to a running sum of weighted count values;
  adjustment means coupled to said computing means for varying a periodic rate for said triggering signal, said variable periodic rate corresponding to an Activity Rate Function, where

ACTIVITY RATE FUNCTION =

$$\frac{1}{K} \times \frac{60}{\text{CLOCKS}} \times \left[\frac{32768}{328}\right]$$

where K is a scaling factor which varies according to a maximum peak voltage level of an excursion of said pulsatile signal during a prior, predetermined time period; and where $$\text{CLOCKS} = \frac{C}{\text{ACTIVITY COUNT} + D}$$

where

-continued $$C = \frac{(2 \times d)}{e}$$

and $$D = \left(\frac{h}{e}\right)$$

where $$d = \frac{(108 \times U_T \times L_T)}{(L_T - U_T)}$$

and e is selectable in the range three to twelve, and where $$h = \frac{(216 \times U_T)}{(L_T - U_T)}$$

with $L_T$ and $U_T$ corresponding to selected lower and upper rate limits, respectively, where possible values of $L_T$ and $U_T$ and respectively corresponding lower and upper rates are:

| LOWER RATE | $L_T$ |
|---|---|
| 40 PPM | 139 |
| 50 PPM | 119 |
| 60 PPM | 96 |
| 70 PPM | 85 |
| 80 PPM | 74 |
| 90 PPM | 66 |
| UPPER RATE | $U_T$ |
| 100 PPM | 59 |
| 125 PPM | 47 |
| 150 PPM | 39 |
| 175 PPM | 22. |

8. A method of periodically selecting a pacing rate for a variable rate cardiac pacemaker, comprising the steps of:
 (a) producing a pulsatile activity signal indicative of a patient's activity;
 (b) defining a plurality of levels of physical activity of a patient, each of said levels having a weight factor associated therewith;
 (c) upon detection of said patient's activity at one of said plurality of levels, adding said weight factor associated with said one level to an Activity Count value;
 (d) performing step (c) repeatedly over a predetermined time interval;
 (e) upon expiration of said time interval, selecting said pacing rate proportional to said Activity Count value at expiration of said time interval; and
 (f) delivering pacing pulses to said patient's heart at said selected pacing rate.

* * * * *

UNITED STATES PATENT AND TRADEMARK OFFICE
CERTIFICATE OF CORRECTION

PATENT NO. : 5,243,979

DATED : September 14, 1993

INVENTOR(S) : Paul M. Stein, and David L. Thompson

It is certified that error appears in the above-indentified patent and that said Letters Patent is hereby corrected as shown below:

Column 3, Line 61-62, after "pacemaker", add --10--.

Column 8, Line 46, delete "V = axis", and insert in its place --V=0 axis --.

Column 9, Line 6, delete "weighted 10", and insert in its place --weighted--.

Column 9, Line 59, delete "$L_{96}$", and insert in its place --$L_T$--.

Column 12, Line 10, after "pacemaker", add --10--.

Column 14, Line 27, delete "$V_I$", and insert in its place --$V_1$--.

Column 14, Line 32, delete "$T_I$", and insert in its place --$T_1$--.

Column 14, Line 58, delete "$T_I$", and insert in its place --$T_1$--.

Column 14, Line 61, delete "$W_I$", and insert in its place --$W_1$--.

Column 14, Line 63, delete "$T_I$", and insert in its place --$T_1$--.

Column 15, Line 8, delete "$T_I$", and insert in its place --$T_1$--.

Column 15, Line 10, delete "$W_I$", and insert in its place --$W_1$--.

Column 15, Line 14, delete "$T_I$", and insert in its place --$T_1$--.

UNITED STATES PATENT AND TRADEMARK OFFICE
CERTIFICATE OF CORRECTION

PATENT NO. : 5,243,979
DATED : September 14, 1993
INVENTOR(S) : Paul M. Stein, and David L. Thompson It is certified that error appears in the above-indentified patent and that said Letters Patent is hereby corrected as shown below:

Column 15, Line 59, delete "$U_{96}$", and insert in its place --$U_r$--.

Column 16, Line 30, delete "$T_I$", and insert in its place --$T_1$--.

Column 16, Line 31, delete "$T_I$", and insert in its place --$T_1$--.

Column 16, line 31, delete "$V_1$" insert in its place --$V_1$--.

Column 16, Line 32, delete "$V_N$", and insert in its place --$<V_N$--.

Column 16, Line 33, delete "$T_I$", and insert in its place --$T_1$--.

Column 16, Line 34, delete "$\{W_I...W_N 56$", and insert in its place --$\{W_1...W_N\}$ Column 16, Line 35, delete "$W_N$", and insert in its place --$<W_N$--.

Column 16, Line 36, delete "$T_I$", and insert in its place --$T_1$--.

Signed and Sealed this

Eighteenth Day of October, 1994

BRUCE LEHMAN

Attest:

*Attesting Officer*    *Commissioner of Patents and Trademarks*